(12) United States Patent
Fuchs et al.

(10) Patent No.: US 7,195,598 B2
(45) Date of Patent: Mar. 27, 2007

(54) METHOD FOR DETERMINING THE EFFECTIVENESS OF A MEDICAL THERAPY BY ANALYSIS OF COLLATERAL VESSELS

(75) Inventors: Friedrich Fuchs, Rottenbach (DE); Rainer Kuth, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 693 days.

(21) Appl. No.: 10/444,280

(22) Filed: May 23, 2003

(65) Prior Publication Data

US 2004/0236234 A1 Nov. 25, 2004

(51) Int. Cl.
*A61B 5/00* (2006.01)
*A61B 5/02* (2006.01)
(52) U.S. Cl. ...................... 600/504; 600/505
(58) Field of Classification Search ............... 600/500
See application file for complete search history.

(56) References Cited

U.S. PATENT DOCUMENTS 6,451,303 B1* 9/2002 Whitehouse et al. ...... 424/85.1
6,878,371 B2* 4/2005 Ueno et al. ................ 424/93.1

OTHER PUBLICATIONS

Murohara, T. et al., "Nitric Oxide Synthase Modulates Angiogenesis in Response to Tissue Ischemia," Journal of Clinical Investigation, vol. 101(11): 2567-2578, 1998.*
Greil et al., "Effect of Acquisition Parameters on the Accuracy of Velocity Encoded Cine Magnetic Resonance Imaging Blood Flow Measurements," Journal of Magnetic Resonance Imaging, vol. 15: 47-54, 2002.*
Yang, H.T. et al., "bFGF Increases Collateral Blood Flow in Rats With Femoral Arterial Ligation," American Journal of Physiology—Heart and Circulatory Physiology, vol. 278: H85-H93, 2000.*

* cited by examiner

*Primary Examiner*—Robert L. Nasser
(74) *Attorney, Agent, or Firm*—Schiff Hardin LLP

(57) ABSTRACT

In a method for determining the effectiveness of a therapy for alleviating a constriction in a blood vessel, the functioning of collateral vessels naturally formed at the constriction is analyzed. The analysis takes place by making a blood flow measurement at the vessel in which the constriction is present, or at a complementary vessel, with the patient experiencing two different stress conditions. The flow measurement can ensue by magnetic resonance or using ultrasound. Comparison of the stress-dependent blood flow to a reference is then undertaken to determine whether the collateral vessels are functioning effectively, and thus whether the treatment for alleviating the constriction is effective.

11 Claims, 1 Drawing Sheet

METHOD FOR DETERMINING THE EFFECTIVENESS OF A MEDICAL THERAPY BY ANALYSIS OF COLLATERAL VESSELS

BACKGROUND OF THE INVENTION

1. Field of the Invention

The present invention is directed to a method for determining the effectiveness of a medical therapy administered to a patient, and in particular to a method for determining the effectiveness of a medical therapy for treating diseases of blood vessels.

2. Description of the Prior Art

Diseases associated with blood vessels are a common condition, and often have serious consequences, particularly in patients of advanced age. Many therapies are known for treating such diseases, for example, medications that dilate the blood vessels (Pentoxyfillin, Dusodril, etc.) the insertion of stents (small supporting structures for the vessel that are introduced internally within the vessel), balloon dilation (the use of an inflatable balloon at a catheter tip introduced into a vessel to widen a constriction, as well as surgical bypasses (an artificial detour that is surgically produced around a constriction).

A constriction in a vessel usually results in the natural formation one or more bypasses, referred to as collaterals or collateral vessels. These are new vessels that the body forms in an effort to alleviate the effects of the constriction, in which blood can flow around the constriction. Dependent on the general vitality of the patient (age, genetic factors, tobacco use, nutrition, etc.) the effectiveness of the natural formation of these collateral vessels differs greatly. Currently, there are no diagnostic methods available which are able to provide quantitative information with regard to the clinical relevance of a vessel constriction, taking the bypass circulation into consideration.

SUMMARY OF THE INVENTION

It is an object of the present invention to provide a method for analyzing the effectiveness of a medical therapy employed to treat a blood vessel constriction, which allows an analysis of collateral vessels, and more specifically blood flow through such collateral vessels, to be taken into account.

The above object is achieved in accordance with the principles of the present invention in a method for analyzing the function of collateral vessels that have formed in a blood vessel of a living subject due to a constriction in the blood vessel, wherein blood flow in the proximity of the constriction is determined, or blood flow in the complementary vessel is determined, for at least two stress conditions of the subject, and a criterion representing the function of the collateral vessels is determined from an analysis of the stress-dependent blood flow measurements.

The blood flow measurements can be made, for example, using Doppler ultrasound or magnetic resonance imaging. Doppler ultrasound allows a quantitative flow measurement to be made in certain vessels that are accessible to ultrasound measurement dependent on their position and size. Known methods for determining flow from ultrasound data can be employed, such as the uniform sensitivity method or the velocity profile method. Flow measurements using magnetic resonance allow the measurement of blood flow in virtually any vessel, with or without contrast agent, with the only limitation being that the vessel in which the blood flows is measured must have a minimum diameter.

Techniques known from magnetic resonance angiography, such as time-of-flight angiography and phase-contrast angiography, can be used to obtain a flow measurement by means of magnetic resonance.

As noted above, the blood flow can be measured in the actual vessel wherein the constriction is present, or in the complementary blood vessel (also referred to as the corresponding vessel) of the vessel containing the constriction. The complementary or corresponding blood vessel means the vessel in which blood flows in an opposite direction relative to the heart compared to the vessel in which the constriction is present. The corresponding blood vessel in the case of an artery is the vein that returns the blood to the heart that flowed in the artery in question. The corresponding vessel for a vein is the corresponding artery.

At a constriction, bypass vessels (collateral vessels) usually will have formed naturally, which will afford an adequate blood flow in unstressed conditions. Such collateral vessels generally have only a microscopic diameter, and therefore a direct measurement of blood circulation in those collateral vessels cannot be obtained or objectively evaluated. Typically, such bypass vessels are insufficient to afford adequate blood flow under stress, and therefore under stress conditions the organ receiving the blood flow will be undersupplied. An example is the so-called "display window" disease wherein a patient must repeatedly stand still because the patient's leg is undersupplied when the patient is walking and the patient then experiences pain, which recedes when the patient stops walking and the stress is removed and the leg is again adequately supplied with blood.

Therefore, in accordance with the invention in order to determine the collateral circulation the blood flow is measured under different physical stress conditions. The blood flow distally from a vessel constriction can be compared to a reference as a function of the stress. The reference can be a measurement made at the other side of the body of the same patient, or can be obtained from a databank of measurements made for similar persons (i.e., persons of similar age, weight, medical history, etc.).

As a result of such measurements, the effectiveness of a particular medical therapy administered for treating or alleviating the effects of the constriction can be monitored. From this evaluation of the effectiveness of the therapy, patients who are not benefiting from a particular therapy can be identified, and the ineffective therapy can be terminated and a different therapy substituted. The effectiveness of the substitute therapy can be analyzed in the same way. Since medications administered in connection with certain therapies can be expensive, the ability to monitor the effectiveness of the therapy not only allows an ineffective therapy to be identified and changed, but also allows management of health care costs by allowing an identification of when an expensive medication is ineffective, and therefore not needed.

DESCRIPTION OF THE PREFERRED EMBODIMENTS

Figure 1:
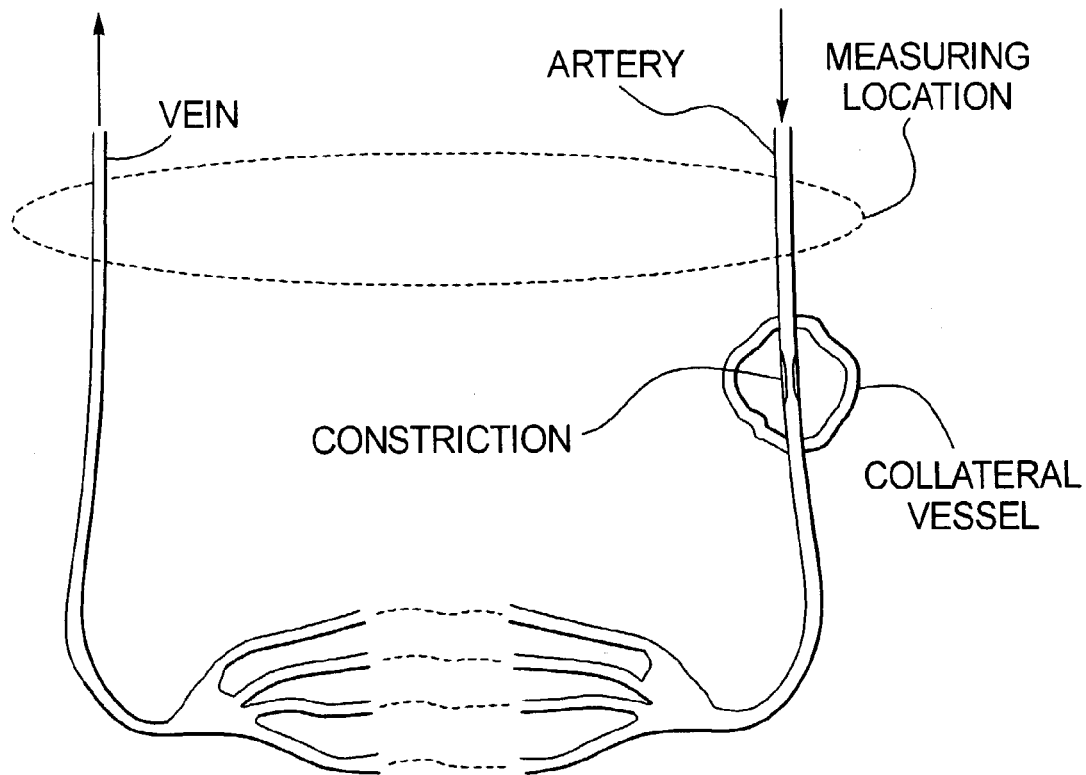
FIG. 1 schematically illustrates a vessel containing an constriction and a collateral vessel formed to by bypass the constriction, and the complementary or corresponding vessel.

In the exemplary embodiment shown in FIG. 1, a vessel, in this case an artery, has a constriction therein, which has resulted in the generation of a schematically-indicated collateral vessel or bypass. The corresponding vessel, in this case the vein via which blood flowing in the artery is returned, is also shown. It will be understood that the principles of the present invention would apply equally if the constriction were in the vein, in which case the artery would be the corresponding vessel.

In accordance with the invention, blood flow is measured in the artery and in the complementary vein. The flow measurement is made using a suitable, known flow measurement technique, such as Doppler ultrasound or magnetic resonance flow measurement. If a magnetic resonance measurement is employed, this can be done with or without contrast agent. At least two blood flow measurements of the patient are obtained, with the patient being subjected to different levels of physical stress at the time of the respective measurements. For example, one measurement can be made with the patient at rest and another measurement can be made while the patient is undergoing exercise. Another alternative is to create the stress by administering a medication that temporarily raises the patient's pulse, such as Pentoxyfillin and new endothelagonists. Creating the stress by administering medication has the advantage that the stress will be substantially independent of the individual patient (since individual patients may have different fitness levels, thereby affecting the degree of exercise needed to create a particular stress level), and also does not require cooperation of the patient to undergo the exercise. The flow measurements can be made in the vessel containing the constriction, which is the artery in the embodiment of FIG. 1, or in the complementary vessel, which is the vein in FIG. 1. This is indicated in FIG. 1 by the dashed line designated measuring location.

The blood flow distally from the vessel constriction is compared as a function of the stress to a reference. The reference can be a measurement made at the other side of the body of the same patient, or can be obtained from a databank of measurements obtained from patients of similar age, weight, medical history, etc.

Figure 2:
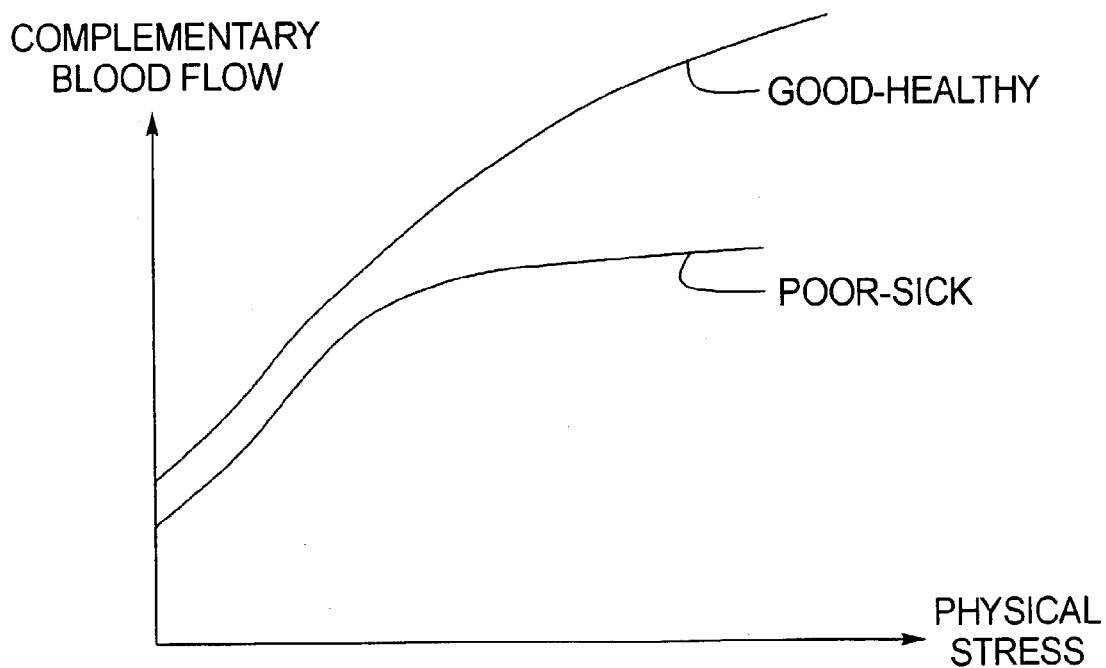
FIG. 2 is a graph showing complementary blood flow relative to physical stress, for a healthy patient and for a diseased patient.

FIG. 2 shows, as an example, the functional relationship between complementary blood flow and physical stress, which can be measured, for example, as heartbeats per minute. The upper curve indicates the relationship obtained from a healthy person, and the lower curve represents the relationship for a person experiencing a disease that has produced a constriction with inadequate collateral vessels.

For determining the effectiveness of a vessel-dilating medication, for example, the aforementioned function can be measured at defined locations, or at a number of locations, after the administration of the medication. The effectiveness of such a vessel-dilating medication thus can be determined for the individual patient, so that only a patient who will in fact benefit from the administration of this medication will be treated with the medication. This also reduces health care costs, because an expensive but ineffective medication will be prescribed at all, if the above-described measurements are made early in the treatment of the patient, or if such a medication is prescribed and is then determined to be ineffective, it's use for a particular patient can be discontinued.

The inventive method also can be employed, for example, to determine whether a particular patient would benefit from receiving beta blockers. In general, the probability that a particular medication will be effective for a particular patient can be predicted only on the basis of statistical information, but the inventive method allows an actual determination for a particular patient to be made regarding such effectiveness.

The inventive method also can be employed to determine whether a constriction that has been treated with some type of ablation procedure or balloon catheter procedure is remaining open to a satisfactory degree, or whether the constriction has re-occurred, in which case implantation of a stent may be advisable.

The need for such additional measures such as stent implantation can be determined in advance of the patient experiencing symptoms, which may be life-threatening, which would then be diagnosed as making the patient a candidate for stent implantation.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for analyzing functioning of a collateral vessel formed at a constriction in a blood vessel of a living subject, comprising the steps of:
   determining blood flow in said collateral vessel of said living subject at a measuring location selected from the group consisting of in the proximity of said constriction and in a complementary blood vessel to the blood vessel containing the constriction, with said living subject in at least two different stress conditions; and
   evaluating said functioning of said collateral vessel dependent on said blood flow relative to stress.

2. A method as claimed in claim 1 comprising determining said functioning of said collateral vessel by a comparison of said blood flow relative to stress with respect to a reference value.

3. A method as claimed in claim 2 comprising obtaining said reference value by making a blood flow measurement at a blood vessel disposed at an opposite side of said living subject from said blood vessel containing said constriction.

4. A method as claimed in claim 2 comprising obtaining said reference value from a table of stress-dependent blood flow values on a group of subjects comparable to said living subject.

5. A method as claimed in claim 1 comprising inducing said stress conditions by administering medication to said living subject.

6. A method as claimed in claim 1 comprising inducing said stress conditions by said living subject undergoing physical activity.

7. A method as claimed in claim 6 wherein at least one of said stress conditions is a static stress condition.

8. A method as claimed in claim 7 wherein another of said stress conditions is a dynamic stress condition.

9. A method as claimed in claim 1 comprising measuring said blood flow by magnetic resonance.

10. A method as claimed in claim 1 comprising measuring said blood flow by an ultrasound measurement.

11. A method as claimed in claim 1 comprising the additional step of evaluating effectiveness of a treatment for alleviating said constriction, administered to said living subject, from said criterion for the functioning of said collateral vessel.

* * * * *